United States Patent [19]

Chappell

[11] Patent Number: 5,415,887

[45] Date of Patent: May 16, 1995

[54] WATER-BASE FILM FORMING COMPOSITION FOR INHIBITING GROWTH OF MOLD AND FUNGUS

[75] Inventor: Rulon A. Chappell, North St. Paul, Minn.

[73] Assignee: Qualcepts Nutrients, Inc., Minneapolis, Minn.

[21] Appl. No.: 264,991

[22] Filed: Jun. 24, 1994

[51] Int. Cl.⁶ .................. B05D 1/00; A01N 25/00
[52] U.S. Cl. ........................... 427/8; 427/2.1; 427/383.7; 424/409
[58] Field of Search ............ 427/258, 260, 261, 322, 427/2.1, 8, 384; 424/405, 407, 409, 411; 106/15.05

[56] References Cited

U.S. PATENT DOCUMENTS

| | | | |
|---|---|---|---|
| 2,379,294 | 6/1945 | Gooding | 99/224 |
| 2,866,817 | 12/1958 | Montagna et al. | 260/526 |
| 2,866,819 | 12/1958 | Montagna et al. | 260/526 |
| 3,173,948 | 3/1965 | Probst et al. | 260/526 |
| 4,055,617 | 10/1977 | Taga et al. | 264/141 |
| 4,847,067 | 7/1989 | Thomas | 424/639 |
| 4,935,232 | 6/1990 | McIntosh | 424/78 |
| 5,141,803 | 8/1992 | Pregozen | 428/288 |

OTHER PUBLICATIONS

The Merck Index, 11th Edition, 1989; pp. 1217 and 1375.

*Primary Examiner*—Shrive Beck
*Assistant Examiner*—Fred J. Parker
*Attorney, Agent, or Firm*—Haugen and Nikolai

[57] ABSTRACT

An aqueous-based film-forming composition for use on wall surfaces for inhibiting growth of mold and fungus in food processing facilities, particularly facilities for processing dairy products such as cheese. The formulation includes, as significant components, cellulose gum in a range of from 2% to 5% by weight, potassium sorbate in a range of from 1% to 2% by weight, acetic acid (glacial) in an amount of from 0.1% to 0.5% by weight, balance water.

2 Claims, No Drawings

WATER-BASE FILM FORMING COMPOSITION FOR INHIBITING GROWTH OF MOLD AND FUNGUS

BACKGROUND OF THE INVENTION

The present invention relates generally to an improved aqueous based solution for forming a film composition on wall surfaces for the purpose of inhibiting growth of mold and fungus in food processing facilities. More specifically, the present invention relates to an improved water-based film forming composition for inhibiting growth of mold and fungus on walls and other surfaces of facilities for processing dairy products such as cheese and the like which are intended for human consumption. The present formulation is stable, has a reasonable shelf-life, and with the working solution having a reasonably extensive pot-life. Each of the components present in the formulation is approved by the F.D.A. for applications which include incidental contact with food.

SUMMARY OF THE INVENTION

Briefly, in accordance with the present invention, a clear water-based film-forming solution is provided which has been found to be effective in retarding the growth of microorganisms and fungi on walls and other surfaces of food processing facilities. The formulation includes, as active ingredients, cellulose gum, potassium sorbate, and acetic acid. The cellulose gum (also frequently referred to as carboxymethylcellulose and/or sodium carboxymethylcellulose) is the designation for the purified form of carboxymethylcellulose, with this material functioning as a dispersing agent as well as a film former when the water solvent has been evaporated. Potassium sorbate has utility as a growth inhibitor for microorganisms and various fungi, with potassium sorbate functioning further as a buffer to assist in control of the pH of the solution. Acetic acid is employed to control pH as well as to provide the material with an easily recognizable and non-harmful odor in order to apprise the applicator of the existence of areas to which the formulation has already been applied. In the working solution, the pH is preferably held at a level of about 5.

As a further consideration, each of the components in the solution is approved for use in an environment where food intended for human consumption is being processed.

Therefore, it is a primary object of the present invention to provide an improved aqueous based film forming material for use in inhibiting the growth of microorganisms and fungus in and on wall surfaces within a food processing facility.

It is a further object of the present invention to provide an improved aqueous film forming solution which includes cellulose gum, potassium sorbate and acetic acid.

It is yet a further object of the present invention to provide an improved film forming solution which is clear and colorless, and which, upon drying, provides a film which inhibits the growth of microorganisms and fungus, and which further contains, in its liquid form, an odorant which enables the applicator to be aware of the zones which have previously been treated with the film forming solution.

Other and further objects of the present invention will become apparent to those skilled in the art upon a study of the following specification and appended claims.

DESCRIPTION OF THE PREFERRED EMBODIMENT

In accordance with the preferred modification of the present invention, a series of examples which set forth the features of the invention are set forth hereinbelow.

EXAMPLE I

A water-based coating solution was prepared having the following formulation:

| Ingredient | Percent by Weight |
| --- | --- |
| Cellulose gum (Methocel) | 3.5% |
| Potassium sorbate | 1.5% |
| Acetic acid (glacial) | 0.2% |
| Water | balance of 94.8%. |

Cellulose gum is available commercially under the trade designation "Methocel" from Dow Chemical Company of Midland, Mich. Other forms of cellulose gum may also be employed. Cellulose gum is prepared commercially by the reaction of alkali cellulose with sodium chloroacetate, with the commercial product normally containing about 0.5 carboxymethyl groups per $C_6$ unit. Cellulose gum, which is soluble in both cold and hot water, in its purified form, is approved for use in foods.

GENERAL EXAMPLE

In accordance with the present invention, the cellulose gum component functions as a dispersing agent and film former upon evaporative loss of the water. Cellulose gum, being food approved, is useful in environments where contact, including incidental contact with food is likely. In this connection, the cellulose gum may be employed in the working solutions in ranges from between about 2% and 5% by weight.

Potassium sorbate is useful as a component for inhibiting the growth of microorganisms and fungi. Potassium sorbate further functions as a buffer in the solution, with potassium sorbate in aqueous solution generally having a pH in the range of between about 9 and 9.2. The presence of acetic acid reduces the pH to a more acceptable level, such as in the range of about 5. Working solutions having a pH ranging from between about 5 and 5.5 are generally acceptable and useful. The potassium sorbate is preferably present in the range of 1.5% by weight, although a range from between 1% and 2% by weight may be useful.

Acetic acid (glacial) is utilized to reduce the pH of the solution as well as for the purpose of providing a non-harmful odorant. The applicator, by a simple sense of smell, can determine the location of water-containing film on a wall or other surface. Acetic acid (glacial) is preferably present in a range from between about 0.1% to about 0.5% by weight. The working solutions of the present invention can be prepared with the addition of acetic acid in an amount of between about 0.1% and up to about 0.5% by weight, and with the pH being below 5.5. As indicated above, a pH of about 5 is generally preferred.

APPLICATION TECHNIQUES

The composition for inhibiting growth of mold and fungus of the present invention may be applied by any conventional technique, including paint brush, paint roller, pad applicators, cloth applicators, and the like. The viscosity of the solution is sufficiently high so as to provide adequate adhesion and with adequate cohesive strength being present in the film. Whenever it is desirable to recoat the surface for fresh application of the inhibitor material, the fresh material may be applied directly over the old. Water removal of old films may also be employed.

What is claimed is:

1. A method for inhibiting the growth of microorganisms in and on wall surfaces within a processing facility for dairy products which comprises applying an aqueous film forming composition to said wall surfaces having the following formulation:

| Ingredient | Percent by Weight |
|---|---|
| Carboxymethylcellulose [Cellulose gum (Methocel)] | 2%–5% |
| Potassium sorbate | 1%–2% |
| Acetic acid (glacial) | 0.1%–0.5% |
| Water | balance | and thereafter permitting the formulation to air dry.

2. The method as defined in claim 1 being particularly characterized in that the formulation is as follows:

| Ingredient | Percent by Weight |
|---|---|
| Carboxymethylcellulose | 3.5% |
| Potassium sorbate | 1.5% |
| Acetic acid (glacial) | 0.2% |
| Water | balance of 94.8%. |

* * * * *

UNITED STATES PATENT AND TRADEMARK OFFICE
CERTIFICATE OF CORRECTION

PATENT NO. : 5,415,887
DATED : May 16, 1995
INVENTOR(S) : RULON A. CHAPPELL

It is certified that error appears in the above-indentified patent and that said Letters Patent is hereby corrected as shown below:

Column 4, lines 3 and 4, "[Cellulose gum (Methocel)]" should be deleted.

Signed and Sealed this

Twelfth Day of September, 1995

Attest:

BRUCE LEHMAN

Attesting Officer    Commissioner of Patents and Trademarks